(12) United States Patent
Steinbrenner et al.

(10) Patent No.: US 7,652,183 B2
(45) Date of Patent: Jan. 26, 2010

(54) METHOD FOR PRODUCING ALKYL AROMATIC COMPOUNDS

(75) Inventors: Ulrich Steinbrenner, Nuestadt (DE); Thomas Narbeshuber, Mannheim (DE); Joerg Unger, Boehl-Iggelheim (DE); Peter Zehner, Ludwigshafen (DE); Soeren Zimdahl, Schriesheim (DE); Regina Benfer, Altrip (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 817 days.

(21) Appl. No.: 10/552,434

(22) PCT Filed: Apr. 14, 2004

(86) PCT No.: PCT/EP2004/003928

§ 371 (c)(1),
(2), (4) Date: Oct. 6, 2005

(87) PCT Pub. No.: WO2004/092096

PCT Pub. Date: Oct. 28, 2004

(65) Prior Publication Data

US 2006/0241328 A1    Oct. 26, 2006

(30) Foreign Application Priority Data

Apr. 15, 2003  (DE) ................. 103 17 294

(51) Int. Cl.
  *C07C 2/66* (2006.01)
(52) U.S. Cl. ..................................... 585/449; 585/447
(58) Field of Classification Search ................ 585/449, 585/447
  See application file for complete search history.

(56) References Cited

U.S. PATENT DOCUMENTS 3,207,800 A * 9/1965 Williamson et al. ......... 585/449
5,198,595 A * 3/1993 Lee et al. .................... 585/467

FOREIGN PATENT DOCUMENTS

| DE | 17 68 021 | 9/1971 |
| DE | 24 13 444 | 10/1974 |
| DE | 199 32 060 | 1/2001 |
| WO | 00/39058 | 7/2000 |
| WO | 02/14266 | 2/2002 |
| WO | 02/44114 | 6/2002 |

* cited by examiner

*Primary Examiner*—Thuan Dinh Dang
(74) *Attorney, Agent, or Firm*—Oblon, Spivak, McClelland, Maier & Neustadt, L.L.P.

(57) ABSTRACT

In a process for the preparation of alkylaromatic compounds by reacting $C_{3\text{-}30}$-olefins, or alcohols from which $C_{3\text{-}30}$-olefins are formed under the reaction conditions, with an aromatic hydrocarbon in the presence of an alkylation catalyst, the reaction is carried out in a reactor cascade of at least two reactors, where each of the reactors comprises the alkylation catalyst, at least 80% of the aromatic hydrocarbon are fed into the first reactor of the reactor cascade, and at least 40% of the olefins are intermediately fed in after the first reactor.

10 Claims, No Drawings

METHOD FOR PRODUCING ALKYL AROMATIC COMPOUNDS

The invention relates to a process for the preparation of alkylaromatic compounds by reacting $C_{3-30}$-olefins, or alcohols from which $C_{3-30}$-olefins are formed under the reaction conditions, with an aromatic hydrocarbon in the presence of an alkylation catalyst. In addition, the invention relates to a process for the preparation of alkylarylsulfonates in which the resulting alkylaromatic compounds are further reacted.

Alkylbenzenesulfonates (ABS) have been used for a long time as surfactants in detergents and cleaners. Following the use initially of those surfactants based on tetrapropylene, which, however, had poor biodegradability, alkylbenzenesulfonates which are as linear as possible (LAS) have since been prepared and used. However, linear alkylbenzenesulfonates do not have adequate property profiles in all areas of application.

For this reason, partially branched alkylbenzenesulfonates have been developed which exhibit an improved property profile. In particular, they exhibit good low-temperature washing properties and compatibility with hard water. WO 02/14266 describes such alkylarylsulfonates and processes for their preparation. The preparation takes place by reaction of a $C_4$-olefin mixture over a metathesis catalyst, dimerization of the $C_{5/6}$-olefins obtained from the metathesis, alkylation of aromatic hydrocarbons with the resulting $C_{10-12}$-olefins, sulfonation of the alkylaromatic compounds and optional neutralization. The process allows a suitable degree of branching in the alkyl radicals to be set. Excessive branching impairs the biodegradability of the products, whereas products which are too linear have a negative effect on the viscosity and the solubility of the sulfonates.

WO 02/44114 also describes processes for the preparation of alkylarylsulfonates. The partially branched alkylaryl compounds required for this purpose are obtained by alkylation of aromatic hydrocarbons with special olefin mixtures. The alkylation is carried out here in the presence of a zeolite of the faujasite type as alkylation catalyst.

In the alkylation processes, the reaction generally takes place in a single reactor in a continuous or discontinuous procedure. Aromatic hydrocarbon and olefin are fed into the reactor at one position. This procedure does not always lead to adequate service lives of the catalyst. In particular, the activity of the catalyst can decrease over prolonged periods of time.

It is an object of the present invention to provide a process for the alkylation of aromatic hydrocarbons which avoids the disadvantages of the existing processes and, in particular, increases the service life of the catalyst.

We have found that this object is achieved according to the invention by a process for the preparation of alkylaromatic compounds by reacting $C_{3-30}$-olefins, or alcohols from which $C_{3-30}$-olefins are formed under the reaction conditions, with an aromatic hydrocarbon in the presence of an alkylation catalyst, which comprises carrying out the reaction in a reactor cascade of at least two reactors, where each of the reactors comprises the alkylation catalyst, at least 80% of the aromatic hydrocarbon are fed into the first reactor of the reactor cascade, and at least 40% of the olefins are intermediately fed in after the first reactor.

It has been found according to the invention that with a reaction in a reactor cascade with intermediate feed of the olefins it is possible to considerably improve the catalyst service lives. More product can thereby be prepared before the catalyst is regenerated.

According to the invention, the reactor cascade is constructed from at least two serially connected reactors. Preference is given to using at least three reactors. The greatest number of reactors here is limited only by practical considerations. Preferably, the number of reactors is 3 to 20, particularly preferably 3 to 10.

The reactors are connected in series so that the exit stream from the first reactor is passed to the second reactor. The same applies for the other reactors.

The reactors preferably have the characteristics of a stirred-tank reactor. This means that, in the reactors, circulation of the introduced substances takes place, which is preferably at least twice, particularly preferably at least three times, in particular at least five times, the feed stream. The individual reactors can thus be stirred-tank reactors, loop reactors, reactors with external circulation, jet loop reactors, and reactors with moving or migrating beds.

In the process according to the invention, at least 80% of the aromatic hydrocarbon are fed into the first reactor of the reactor cascade. Preferably, at least 90% of the aromatic hydrocarbon are fed into the first reactor, particularly preferably essentially the entire aromatic hydrocarbons or the entire aromatic hydrocarbons.

At least 40% of the olefins are intermediately fed in after the first reactor. Accordingly, at most 60% of the olefins are fed into the first reactor of the reactor cascade. The intermediate feed takes place, apart from the first reactor of the reactor cascade, in at least one further reactor of the reactor cascade. An intermediate feed particularly preferably takes place before each of the reactors in the reactor cascade. The proportions of the olefin which are intermediately fed in before each reactor or in each reactor can be freely chosen. Preferably, the feed streams differ in each case by at most 50%. Particular preference is given to (intermediately) feeding in approximately equal proportions of the olefin into each reactor. In particular, in each case equal proportions of the olefin are (intermediately) fed into each reactor. Preferably, the olefin is well stirred in or mixed in during the feed. This is effected, for example, by active or passive elements, for example by pumps, static mixers or inert beds. Preferably, the feed is metered in or before the circulation pump(s).

According to the invention, each of the reactors comprises the alkylation catalyst. Preferably, the amounts of catalyst in the individual reactors differ by at most 50%, particularly preferably at most 20%, in particular at most 10%, based on the reactor with the largest amount of catalyst. This means that in each case the difference between the amount of catalyst in the reactor with the largest amount of catalyst and each of the other reactors, divided by the amount of catalyst in the reactor with the largest amount of catalyst, is at most 50%, particularly preferably at most 20%, in particular at most 10%. All of the catalysts particularly preferably comprise the same amount of catalyst.

The process according to the invention leads—averaged over the entire amount of catalyst—to improved catalyst service lives and thus more product being obtained before the catalyst is regenerated.

The type of intermediate feed can be chosen freely. The reactors are typically connected together using connection pipes. Pumps and branches can be integrated into these connections in order to be able to change the order in which the reactors are connected. The olefin intermediate feeds can then take place independently of the connection of the individual reactors with one another in a separate feed stream in each case into the reactor, or the intermediate feeds can take place before the respective reactor so that the mixture to be reacted is introduced into the reactor through only one pipe. Corresponding geometries are known to the person skilled in the art.

The olefin feed is controlled by means of apparatus in a manner known per se using individual pumps, valves, nozzles, diaphragms, orifices or other suitable devices.

According to the present invention, it is not absolutely necessary for each reactor in which there is a feed point for the olefin to be constructed as an individual unit, such as, for example, as a stirred-tank reactor. It is also possible to use constructive configurations of a reactor which satisfy the function of a serial connection of two or more reactor elements. It is therefore also possible to use an individual reactor, in particular a fixed-bed reactor, which is divided into at least two, preferably at least three, segments by suitable internals such as perforated diaphragms or sieve plates. In addition, it is possible to use stirred columns with more than one stage and flow tubes each with two or more feed points.

The control of the addition of the olefins can be adapted to the practical requirements. For example, the amount of added olefin can be matched to the amount of catalyst present in the respective reactor and to the respective catalyst state (deactivation). The addition is preferably controlled such that, in each reactor, based on the amount of catalyst, the same incremental productivity is achieved. The continuous controls of the additions of the olefins can be adapted to the respective conversion within the reactor. Accordingly, according to one embodiment of the invention, the olefin is intermediately fed in before each of the reactors and the amount of olefin intermediately fed in in each case is controlled such that, in each reactor, the same incremental productivity is achieved, based on the respective amount of catalyst. This ensures that the amount of olefin added in each case is adapted to the amount of catalyst present in the respective stage or in the respective reactor if the catalyst is not equally distributed over all stages or reactors. The amount of olefin added is preferably adjusted so that, in each reactor, the same increase in conversion product is achieved, based on the respective amount of catalyst. This is described by the expression "equal incremental productivity". Expressed another way, based on the respective amount of catalyst, the product yield is increased uniformly in each reactor such that the same number of conversions take place over the respective catalyst per unit of time.

If the catalysts present in the various reactors have a different degree of deactivation, this can be compensated accordingly by controlling the amount of olefin feed.

If the amounts of catalyst in the reactors differ by preferably at most 50%, particularly preferably at most 20%, in particular at most 10%, based on the reactor with the largest amount of catalyst, this applies accordingly to the olefin feed if the catalysts in the reactors have the same degree of deactivation. Correspondingly, the deviation of the smallest olefin content in a reactor from the largest olefin content in a reactor is at most 50%, particularly preferably at most 20%, in particular at most 10%, of the largest olefin content. The added amounts of the olefin intermediate feed are thus adapted to the amounts of catalyst present in each case.

According to the invention, catalyst and olefin are particularly preferably uniformly distributed over all reactors or (intermediately) fed into all reactors. Nevertheless, the deviations mentioned above are possible.

Various independent preferred embodiments of the process according to the invention are described below, assuming a reactor cascade of n reactors. The first reactor in which the reaction starts is referred to here as reactor 1. Higher numbers designate reactors which are provided further downstream in the reactor cascade.

In order to ensure uniform deactivation of all reactors, after a time, which is ideally 1/n of the service life, the cascade can be rotated by one reactor, i.e. reactor 1 moves to the position of reactor 2, reactor 2 to the position of reactor 3, ..., reactor n−1 to the position of reactor n and reactor n to the position of reactor 1. Of course, other permutations are conceivable— e.g. in the case of 5 reactors 1⇒3, 2⇒4, 3⇒5, 4⇒1, 5⇒2—which lead to each catalyst bed spending approximately the same time at each position in the cascade.

According to the invention, the order of the reactors within the cascade can thus be changed at time intervals such that each reactor assumes each of the positions within the cascade for the same period of time. Deviations of up to 25%, preferably up to 10%, in particular up to 5%, of this pregiven value are intended to fall within the expression "same period of time".

Only incomplete permutations are also possible, e.g. by exchanging 1 with n, 2 with n−1 etc. Likewise, the exchange can take place not only after a fixed time, but also earlier or later as deactivation of the catalyst increases.

Since it has been found that in the case of cascade-like or series-like connection, the catalyst in reactor 1 was deactivated the least, and that in reactor n was deactivated the most, it is alternatively possible to introduce less catalyst into reactor 1 than into reactor 2, and to introduce less catalyst into reactor 2 than into reactor 3 etc., in order to achieve a fairly uniform deactivation of all beds.

It is also possible to dispense with uniform deactivation. For reasons of efficiency when changing the catalyst or when regenerating the catalyst of a large-scale plant, it is often advantageous not to have to replace or regenerate the entire catalyst mass in one operation. In this case, for example, the rearrangement of the reactors could be omitted and the catalyst in reactor n changed or regenerated more often, and the catalyst in reactor 1 changed or regenerated less often. Here, the conversion after each reactor can expediently be determined. If this falls too far below, then the catalyst in this reactor must be changed. The limit is typically between 95% and 98% conversion.

Whether and how the reactors are newly connected in operation, in which ratio the catalyst mass and the olefin intermediate feeds are divided over the individual reactors is governed by practical requirements. The optimum most favored here can be readily determined using a suitable experimental plan for a defined catalyst and a defined olefin.

Suitable olefins are linear, cyclic and branched monoolefins having 3 to 30 carbon atoms, e.g. propylene, 1-butene, 2-butene, isobutene, 1-pentene, 2-pentene, 3-pentene, cyclopentene, the methylbutenes, the n-hexenes, the methylpentenes, cyclohexene, methylcyclohexene, decenes, undecenes, dodecenes, etc. Preference is given to linear and branched $C_{10}$-$C_{14}$-monoolefins, particularly preferably $C_{10}$-$C_{12}$-monoolefins which have 0 to 3 methyl and/or ethyl branches in the side chain. The olefin preferably originates from the sources given in WO 02/14266 or WO 02/44114.

For example, $C_{10}$-$C_{12}$-olefins can be used which have an average degree of branching in the range from 1 to 2.5, particularly preferably 1 to 2.0, in particular 1 to 1.5 and specifically 1 to 1.2. The degree of branching of a pure olefin is defined here as the number of carbon atoms which are joined to three carbon atoms, plus two times the number of carbon atoms which are joined to 4 carbon atoms. The degree of branching of a pure olefin can be measured here easily following total hydrogenation to the alkane via $^1H$ NMR via the integration of the signals of the methyl groups relative to the methylene and methyne protons.

For mixtures of olefins, the degrees of branching are weighted with the mol percentages, and thus an average degree of branching is calculated.

The molar fractions are determined optimally here by means of gas chromatography.

The nature of the branches in the olefin is here preferably such that, following hydrogenation, less than 10%, preferably less than 5%, particularly preferably less than 1%, of alkanes are obtained which are not types of methyl-, dimethyl-, ethylmethyl- and diethylalkanes. This means that the branches are only methyl and ethyl branches.

The olefins can be obtained by reacting a $C_4$-olefin mixture over a metathesis catalyst to prepare an olefin mixture comprising 2-pentene and/or 3-hexene and optionally separating off 2-pentene and/or 3-hexene, followed by a dimerization of the resulting 2-pentene and/or 3-hexene in the presence of a dimerization catalyst to give a mixture comprising $C_{10\text{-}12}$-olefin, separating off the $C_{10\text{-}12}$-olefins and optionally separating off 5 to 30% by weight, based on the separated-off $C_{10\text{-}12}$-olefins, of low-boiling constituents of the $C_{10\text{-}12}$-olefins.

To prepare a desired degree of branching, it is possible to admix linear olefins with the olefins, or to separate off some of the heavily branched olefins. In the case of admixing, 5 to 60% by weight, for example, of linear olefins can be added.

The metathesis catalyst in the metathesis is preferably chosen from compounds of a metal of subgroups VIb, VIIb or VIIIb of the Periodic Table of the Elements.

The dimerization catalyst used is preferably a catalyst which comprises at least one element of sub-group VIII of the Periodic Table of the Elements.

The $C_4$-olefin mixture used in the metathesis can originate from steam cracker or refinery $C_4$ streams. Firstly, butadiene is separated off from these streams together with acetylenic impurities by extraction and/or selective hydrogenation. Isobutene can then be separated off by reaction with an alcohol in the presence of an acidic catalyst to give an ether. The ether and the alcohol can then be separated off. Oxygenate impurities can then be separated off from the exit stream of the above steps over appropriately selected adsorber materials. This is followed by the metathesis reaction, as is described.

For further individual details of the respective steps, reference may be made to WO 02/14266 and WO 00/39058.

The resulting $C_{10\text{-}12}$-olefin mixtures have an optimum structure/linearity. This means that the degree of branching and the nature of the branching is optimally chosen in order to obtain advantageous alkylaromatic compounds during the alkylation. The $C_{10\text{-}12}$-olefin mixtures to be used optimally can be adjusted, for example, by admixing linear olefins. During the dimerization, particular preference is given to combining a suitable catalyst with a suitable procedure in order to arrive at the optimum $C_{10\text{-}12}$-olefin mixture. In this procedure, the desired structures are obtained directly in the alkylation. In this case, it is possible to dispense with the admixing of linear olefins and the separating off of relatively highly branched olefins. Combinations of the described procedures are also possible.

Alternatively, the olefins or alcohols used for the alkylation can be obtained as follows:

A hydrocarbon mixture is prepared which essentially comprises monoolefins with 4-6 carbon atoms. The monoolefin mixture is then hydroformylated by reaction with carbon monoxide and hydrogen in the presence of a hydroformylation catalyst to give an aldehyde mixture. The aldehyde mixture is then subjected to an aldol condensation to give a mixture of condensed α,β-unsaturated aldehydes. The mixture obtained in this way is then hydrogenated with hydrogen in the presence of a hydrogenation catalyst to give a mixture of saturated alcohols with 10 to 14 carbon atoms. This alcohol mixture can be used directly for the reaction with the aromatic hydrocarbon in the presence of an alkylation catalyst. Alternatively, the resulting alcohol mixture can be dehydrogenated to give an olefin mixture which essentially comprises olefins having 10 to 14 carbon atoms.

The olefin-containing hydrocarbon mixture originally used can be derived from a metathesis of 1-butene and 2-butene.

The olefins used for the alkylation can also be obtained by extraction of predominantly monobranched paraffins from kerosene cuts and subsequent dehydrogenation, by Fischer-Tropsch synthesis of olefins or paraffins, where the paraffins are dehydrogenated, by dimerization of shorter-chain internal olefins or by isomerization of linear olefins or paraffins, the isomerized paraffins being dehydrogenated. Corresponding procedures are described in WO 02/44114.

For the sequence of metathesis and dimerization, reference may also be made to DE-A-199 32 060.

As an alternative to olefins, it is also possible to introduce alcohols into the reaction since, under conditions of aromatic alkylation, these rapidly eliminate $H_2O$ and form olefins. Alcohols are accordingly treated as being equivalent to the olefins formed from them by dehydration.

Suitable aromatics are, for example, benzene, toluene, ethylbenzene and the xylenes, preferably benzene, toluene and ethylbenzene, particularly preferably benzene.

Suitable catalysts are heterogeneous acids, such as, for example, clays, in particular montmorillonite or montmorillonite-containing materials, such as, for example, K10 and K20 from Südchemie, strongly acidic ion exchangers, such as, for example, Amberlyst® 36 or Amberlyst® 15 from Rohm & Haas or Nafion® or Nafion®/silica from DuPont, acidic metal oxides, such as, for example, $M(I)O_3\text{-}M(II)O_2$-$M(I)$=W, Mo and $M(II)$=Zr, Ti, Mn and/or Sn, $Al_2O_3$—$SiO_2$, $TiO_2$—$ZrO_2$, $TiO_2$, $Nb_2O_5$, $Ta_2O_5$, sulfated metal oxides, such as, for example, $ZrO_2$—$SO_3$, $TiO_2$—$SO_3$, $Al_2O_3$—$SO_3$, $WO_3$—$SO_3$, $Nb_2O_5$—$SO_3$, supported heteropolyacids, such as, for example, $PW_{12}$-HPA/$SiO_2$, $PMo_{12}$-HPA/carbon, $P_2W_{18}$-HPA/$TiO_2$ and zeolites.

Preference is given to zeolites of the structure types BIK; BRE, ERI, CHA, DAC, EAB, EDI, EPI, FER, pentasils with MFI or MEL structure, faujasites, such as, for example, Y, LTL, MOR, BEA, GME, HEU, KFI, MAZ, OFF, PAU, RHO, STI. Particular preference is given to L, Y including the USY types, BEA and MOR.

These zeolites are preferably used in the H and/or La form, although traces of Na, K, Mg or Ca may be present depending on the preparation. Partial or complete exchange of the lattice aluminum by B, Ga or Fe is possible.

The catalyst can, for example, be used directly as fine powder in suspension, in the case of zeolites, these are, for example, particle sizes between 100 nm and a few μm. However, in most cases, these catalysts are shaped together with binder materials to give shaped bodies with a diameter of 0.1-5 mm. For use in fixed beds, 1-3 mm are preferred, in suspension 0.001-1 mm, in moving beds 0.1-3 mm. Suitable binders are in particular clays, aluminum oxides, such as, for example, Purals, Sirals and Versals and silica gels. In addition, inert fillers such as $SiO_2$ (e.g. Aerosil from Degussa) can be added.

Examples of suitable shaped bodies are tablets, small strands, rings, ribbed strands, star or wheel extrudates.

The catalysts preferably have specific surface areas of from 30 to 2000 m²/g, preferably 100 to 700 m²/g. The volume of the pores with a diameter of 2-20 nm is typically 0.05-0.5 ml/g, preferably 0.1-0.3 ml/g, that of the pores of 20-200 nm is typically 0.005 to 0.2 ml/g, preferably 0.01 to 0.1 ml/g, and that of the pores of 200-2000 nm is typically 0.05-0.5 ml/g, preferably 0.05 to 0.3 ml/g.

Deactivated catalysts can in most cases be regenerated by burning off in air or depleted air at 250-550° C. Alternatively, a treatment with compounds which have an oxidizing effect at lower temperatures—optionally also in the liquid phase—is possible, in this connection mention is made in particular of $NO_x$, $H_2O_2$ and the halogens. The regeneration can take place directly in the alkylation reactor or externally.

The alkylation preferably takes place in the liquid phase, i.e. without gas phase, which can be achieved by a corresponding system pressure. The pressure is usually the autogeneous pressure (the vapor pressure of the system) or greater. Alkylation temperatures are preferably 100 to 250° C., particularly preferably 120 to 220° C., very particularly preferably 130 to 200° C. Suitable pressures are, for example, in the range from 1 to 35 bar.

When choosing the catalyst, it should be ensured that the formation of compounds which retain carbon atoms with a H/C index of 0 in the alkyl radical is minimized. The H/C index defines here the number of hydrogen atoms per carbon atom in the alkyl radical. The alkylaromatic compounds obtained according to the invention have a characteristic fraction of primary, secondary, tertiary and quaternary carbon atoms in the alkyl radical (side chain). In particular, compounds should be formed which, on average, have one to three carbon atoms with a H/C index of one in the alkyl radical. This can be achieved, in particular, through the choice of suitable catalysts which, on the one hand, suppress the formation of the undesired products as a result of their geometry and, on the other hand, however, permit an adequate rate of reaction.

Preferably, the mixtures of alkylaromatic compounds according to the invention have only a small fraction of carbon atoms in the alkyl radical with a H/C index of zero. Preferably, the fraction of carbon atoms in the alkyl radical with a H/C index of zero is, as an average of all compounds, <15%, particularly preferably <10%. The fraction of carbon atoms, alkyl radical with a H/C index of zero which are bonded simultaneously to the aromatics is preferably at least 80%, particularly preferably at least 90%, in particular at least 95%, of all carbon atoms in the alkyl radical with a H/C index of zero.

Preferably, the mixtures of alkylaromatic compounds obtained according to the invention have, on average, 1 to 3, preferably up to 1 to 2.5, particularly preferably 1 to 2, carbon atoms in the side chain (i.e. without counting the aromatic carbon atoms) with a H/C index of 1. The fraction of compounds with three carbon atoms of this type is preferably less than 30%, particularly preferably less than 20%, in particular less than 10%.

The fraction of carbon atoms which have a certain H/C index can be controlled through suitable choice of the catalyst used. Preferred catalysts with which advantageous H/C distributions are achieved are mordenite, beta-zeolite, L-zeolite and faujasites. Particular preference is given to mordenite and faujasites.

During the reaction, the global—i.e. calculated overall reactors—ratio of aromatic:olefin is usually between 1:1 and 100:1, preferably 2:1 to 20:1 (molar ratio). The global ratio refers here to the ratio of the sum of all aromatic streams in the cascade relative to the sum of all olefin streams in the cascade.

The alkylaromatic compounds obtained can then be sulfonated and neutralized to alkylarylsulfonates. The invention thus also relates to a process for the preparation of alkylaromatic compounds by reacting $C_{3-30}$-olefins, or alcohols from which $C_{3-30}$-olefins are formed under the reaction conditions, with an aromatic hydrocarbon in the presence of an alkylation catalyst, where the reaction is carried out in a reactor cascade of at least two reactors, where each of the reactors comprises the alkylation catalyst, at least 80% of the aromatic hydrocarbon are fed into the first reactor of the reactor cascade, and at least 40% of the olefins are intermediately fed in after the first reactor.

The alkylaryls are converted to alkylarylsulfonates, for example, by sulfonation (e.g. with $SO_3$, oleum, chlorosulfonic acid, preferably with $SO_3$) and neutralization (e.g. with Na, K, $NH_4$, Mg compounds, preferably with Na compounds). Sulfonation and neutralization are described adequately in the literature and are carried out in accordance with the prior art. The sulfonation is preferably carried out in a falling-film reactor, but can also take place in a stirred-tank reactor. Sulfonation with $SO_3$ is preferred over sulfonation with oleum.

The compounds prepared by the described process can be used for the preparation of detergents and cleaners, as is described in WO 02/14266. This literature reference also specifies further ingredients for detergents and cleaners.

The invention is illustrated by the examples below:

EXAMPLES

Preparation of the Catalyst:

4000 g of Mordenite FM-8 (from Uetikon, Si:Al=12.2 mol/mol) were compacted with 2670 g of Pural® SB (from Sasol), 133 g of HCOOH and 3500 g of dist. $H_2O$ in a laboratory kneader for 45 minutes, and extruded to give small strands with a diameter of 1.5 mm. These were calcined for 16 h at 500° C. in air and chipped to a sieve fraction of 0.3-0.5 mm.

The catalyst had a specific surface area according to Langumir of 519±5 $m^2$/g-calculated from the 5 point $N_2$-isotherms in accordance with DIN 66131.

Construction of the Reactors:

Each reactor consisted of a coiled V2A stainless steel pipe with an internal volume of 200 ml, a sieve plate and a 5 μm filter at the exit. The liquid circulation was effected by means of a HPLC pump (from Kontron). The ratio of circulation:feed was always about 10:1. The reactors are heated by a circulatory oven. The catalyst bed of 70 g was located between two inert beds of quartz glass beads each of about 20 g. Each reactor operated at a system pressure of 30 bar, which was applied by the feed pumps (HPLC pumps from Kontron) and maintained by an overflow unit.

Experimental Procedure:

Prior to the start of the experiment, the catalyst chips introduced into the reactors are freshly activated for 5 h at 500° C. with synthetic air and then cooled, and each reactor is filled with pure benzene. They are then heated to 160° C., and circulations and feed are started. The feed streams are purified by a bed of catalyst and 3A molecular sieve maintained at room temperature.

The dodecene used originates from the nickel-catalyzed dimerization of 3-hexene by the variants a) or b) below:

Variant a)

A butadiene-free $C_4$ fraction with a total butene content of 84.2% by weight and a molar ratio of 1-butene to 2-butenes of 1:1.06 is passed continuously at 40° C. and 10 bar over a tubular reactor charged with $Re_2O_7/Al_2O_3$ heterogeneous catalyst. The catalyst space velocity is 4500 kg/$m^2$h in the example. The reaction product is separated by distillation and comprises the following components (data in mass percent):

ethene 1.15%; propene 18.9%, butanes 15.8%, 2-butenes 19.7%, 1-butene 13.3%, isobutene 1.0%, 2-pentene 19.4%, methylbutenes 0.45%, 3-hexene 10.3%.

2-Pentene and 3-hexene are obtained from the product by distillation in purities of >99% by weight.

Variant b)

Continuous Dimerization of 3-hexene in a Fixed-Bed Process

Catalyst: 50% NiO, 34% $SiO_2$, 13% $TiO_2$, 3% $Al_2O_3$ (according to DE 43 39 713) used as 1-1.5 mm chips (100 ml), conditioned for 24 h at 160° C. in $N_2$ Reactor: isothermal, 16 mm Ø reactor WHSV: 0.25 kg/l.h Pressure: 20 to 25 bar Temperature: 100 to 160° C.

| Temperature (°C.) | Feed stock | 100 | 120 | 140 | 160 | 160 | | $C_{12}$ Distillate |
|---|---|---|---|---|---|---|---|---|
| Pressure (bar) | | 20 | 20 | 20 | 25 | 25 | Collected Product | |
| Operating hours | | 12 | 19 | 36 | 60 | 107 | | |
| Liquid produced (g/h) | | 24 | 27 | 27 | 28 | 27 | | |
| Composition (% by wt.) | | | | | | | | |
| $C_6$ | 99.9 | 68.5 | 52.7 | 43.6 | 57.0 | 73.2 | n.d. | 0.1 |
| $C_7$-$C_{11}$ | 0.1 | 0.2 | 0.2 | 0.3 | 0.2 | 0.2 | | — |
| $C_{12}$ | | 25.9 | 38.6 | 44.0 | 35.6 | 23.6 | | 99.9 |
| $C_{13}+$ | | 5.4 | 8.5 | 12.1 | 7.2 | 3.0 | | — |
| Conversion | | 31.4 | 47.2 | 56.4 | 42.9 | 26.7 | | |
| C12 selectivity (% by wt.) | | 82.5 | 81.8 | 78.2 | 83.0 | 88.4 | | |
| S content in the liquid produced (ppm) | <1 | n.d. | n.d. | n.d. | n.d. | n.d. | n.d. | n.d. |

The collected product was distilled to a $C_{12}$ purity of 99.9% by weight.

Analysis:

n-Octane and n-hexadecane is weighed into the samples, the determination of the yield takes place by means of GC-FID (column 50 m DB-5, 0.1 μm film) by the method of the internal standard (benzene based on octane, MLAB on hexadecane). The unreacted olefin is determined by means of GC-MS relative to n-octane as internal standard. The absolute error is about 3% absolute.

Comparative Example 1

A Reactor

A reactor with 70 g of catalyst was used. The benzene:dodecene ratio was 5 mol:1 mol, the feed charge 0.42 g of feed/g of catalyst/h, i.e. 29.4 g/h. The following conversions and yields were measured:

| Run time [h] | Olefin Yield [mol %] | Conversion [mol %] | Benzene Yield [mol %] | Conversion [mol %] |
|---|---|---|---|---|
| 19 | 80% | 100% | 16% | 24% |
| 26 | 83% | 100% | 17% | 25% |
| 42.5 | 84% | 100% | 17% | 25% |
| 50 | 84% | 100% | 17% | 24% |
| 67 | 83% | 100% | 17% | 24% |
| 73.5 | 85% | 100% | 17% | 25% |
| 95.5 | 88% | 100% | 18% | 25% |
| 120 | 87% | 100% | 17% | 24% |
| 139 | 89% | 100% | 18% | 23% |
| 146 | 88% | 100% | 17% | 23% |
| 163 | 83% | 100% | 17% | 22% |
| 170 | 76% | 98% | 15% | 21% |
| 187 | 42% | 50% | 8% | 13% |
| 194 | 39% | 42% | 8% | 18% |

Result:

After about 160 hours, the catalyst was deactivated to such an extent that complete conversion could no longer be achieved.

Example 2

Cascade of 3 Reactors

Three reactors each with 70 g of catalyst were used. The first reactor was charged with a mixture in the ratio benzene:dodecene=15 mol:1 mol and a space velocity of 0.336 g/g/h. The second reactor receives the product stream of the first reactor plus 0.42 g/g/h of dodecene. The third reactor comprises the product stream of the second reactor plus 0.042 g/g/h of dodecene. This corresponds to a total charge of 0.042 g/g/h at a global feed ratio of 5 mol:1 mol. After a run time of 65 h, the main feed stream was switched, by means of valves, from the sequence 1-2-3 to the sequence 2-3-1, after 130 h from 2-3-1 to 3-1-2 and after 195 h from 3-1-2 to 1-2-3. The following conversions and yields were measured over the whole cascade:

| Run time [h] | Olefin Yield [mol %] | Conversion [mol %] | Benzene Yield [mol %] | Conversion [mol %] |
|---|---|---|---|---|
| 20 | 81% | 100% | 16% | 24% |
| 28 | 85% | 100% | 17% | 25% |
| 50 | 86% | 100% | 17% | 24% |
| 65.5 | 85% | 100% | 17% | 24% |
| 72.5 | 86% | 100% | 17% | 25% |
| 94.5 | 90% | 100% | 18% | 25% |
| 117 | 89% | 100% | 18% | 24% |
| 141 | 91% | 100% | 18% | 23% |
| 147 | 89% | 100% | 17% | 23% |
| 161 | 90% | 100% | 17% | 24% |
| 168 | 89% | 100% | 19% | 25% |
| 186 | 91% | 100% | 18% | 22% |
| 192 | 90% | 100% | 18% | 23% |
| 199 | 85% | 98% | 17% | 22% |
| 214 | 54% | 60% | 10% | 14% |
| 230.5 | 20% | 22% | 5% | 7% |

Result:

As well as an increase in the selectivity with regard to dodecene by about 2 percentage points, a catalyst service life which was increased by 22% (199 instead of 163 h) relative to one reactor was recorded.

We claim:

1. A process for the preparation of alkylaromatic compounds by reacting $C_{3-30}$-olefins, or alcohols from which $C_{3-30}$-olefins are formed under the reaction conditions, with an aromatic hydrocarbon in the presence of an alkylation catalyst, which comprises carrying out the reaction in a reactor cascade of at least two reactors, where each of the reactors comprises the alkylation catalyst, at least 80% of the aromatic hydrocarbon is fed into the first reactor of the reactor cascade, and at least 40% of the olefins is intermediately fed in after the first reactor, wherein the order of the reactors within the cascade is changed at time intervals such that each reactor assumes each of the positions within the cascade for the same period of time.

2. The process as claimed in claim 1, wherein the reactor cascade has at least three reactors, and the olefin is intermediately fed in before each of the reactors.

3. The process as claimed in claim 1, wherein in each case equal proportions of the olefin are fed into each reactor.

4. The process as claimed in claim 1, wherein the olefin is intermediately fed in before each of the reactors and the amount of olefin intermediately fed in each case is controlled by individual pumps, valves, nozzles, diaphragms, or orfices such that, in each reactor, the same incremental productivity is achieved, based on the respective amount of catalyst.

5. The process as claimed in claim 1, wherein the reactors in the cascade each have the characteristics of a stirred-tank reactor.

6. The process as claimed in claim 1, wherein the alkylation is carried out in the liquid phase at temperatures in the range from 100 to 250° C.

7. The process as claimed in claim 1, wherein the alkylation catalyst is a heterogeneous catalyst chosen from acidic clays, acidic ion exchangers, acidic metal oxides, sulfated metal oxides, supported heteropolyacids and zeolites.

8. The process as claimed in claim 1, wherein $C_{10-12}$-olefins are used which have an average degree of branching of at least 0.5.

9. The process as claimed in claim 8, wherein the $C_{10-12}$-olefins are obtained by reacting a $C_4$-olefin mixture over a metathesis catalyst to prepare an olefin mixture comprising 2-pentene and/or 3-hexene, and optionally separating off 2-pentene and/or 3-hexene, and dimerizing the resulting 2-pentene and/or 3-hexene in the presence of a dimerization catalyst to give a mixture comprising $C_{10-12}$-olefins, optionally followed by separating off the $C_{10-12}$-olefins and separating off 5 to 30% by weight, based on the separated-off $C_{10-12}$-olefins, of low-boiling constituents of the $C_{10-12}$-olefins.

10. The process for the preparation of alkylarylsulfonates by:
   a) reacting a $C_4$-olefin mixture over a metathesis catalyst to prepare an olefin mixture comprising 2-pentene and/or 3-hexene, and optionally separating off 2-pentene and/or 3-hexene,
   b) dimerizing the 2-pentene and/or 3-hexene obtained in stage a) in the presence of a dimerization catalyst to give a mixture comprising $C_{10-12}$-olefins, optionally separating off the $C_{10-12}$-olefins and separating off 5 to 30% by weight, based on the separated-off $C_{10-12}$-olefins, of low-boiling constituents of the $C_{10-12}$-olefins,
   c) reacting the $C_{10-12}$-olefin mixtures obtained in stage b) with an aromatic hydrocarbon in the presence of an alkylation catalyst to form alkylaromatic compounds, where, prior to the reaction, 0 to 60% by weight, based on the $C_{10-12}$-olefin mixtures obtained in stage b), of linear olefins may additionally be added,
   d) sulfonating the alkylaromatic compounds obtained in stage c) and neutralizing them to give alkylarylsulfonates, where, prior to the sulfonation, 0 to 60% by weight, based on the alkylaromatic compounds obtained in stage c), of linear alkylbenzenes may additionally be added if no such addition has taken place in stage c), and
   e) optionally mixing the alkylarylsulfonates obtained in stage d) with 0 to 60% by weight, based on the alkylarylsulfonates obtained in stage d), of linear alkylarylsulfonates, if no such additions have taken place in stages c) and d);
   wherein the reaction in stage c) is carried out by reacting the $C_{10-12}$-olefin mixtures obtained in stage b) with an aromatic hydrocarbon in the presence of an alkylation catalyst in a reactor cascade of at least two reactors, where each of the reactors comprises the alkylation catalyst, at least 80% of the aromatic hydrocarbon is fed into the first reactor of the reactor cascade, and at least 40% of the olefins is intermediately fed in after the first reactor, wherein the order of the reactors within the cascade is changed at time intervals such that each reactor assumes each of the positions within the cascade for the same period of time.

* * * * *